US012347216B2

(12) United States Patent
Thienphrapa et al.

(10) Patent No.: US 12,347,216 B2
(45) Date of Patent: Jul. 1, 2025

(54) INTERACTIVE ENDOSCOPY FOR INTRAOPERATIVE VIRTUAL ANNOTATION IN VATS AND MINIMALLY INVASIVE SURGERY

(71) Applicant: KONINKLIJKE PHILIPS N.V., Eindhoven (NL)

(72) Inventors: Paul Thienphrapa, Cambridge, MA (US); Torre Michelle Bydlon, Melrose, MA (US); Alvin Chen, Cambridge, MA (US); Prasad Vagdargi, Cambridge, MA (US); William McNamara, Valhalla, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 262 days.

(21) Appl. No.: 17/641,940

(22) PCT Filed: Sep. 11, 2020

(86) PCT No.: PCT/EP2020/075422
§ 371 (c)(1),
(2) Date: Mar. 10, 2022

(87) PCT Pub. No.: WO2021/048326
PCT Pub. Date: Mar. 18, 2021

(65) Prior Publication Data
US 2022/0358773 A1    Nov. 10, 2022

Related U.S. Application Data

(60) Provisional application No. 62/899,365, filed on Sep. 12, 2019.

(51) Int. Cl.
*G06V 20/70* (2022.01)
*A61B 1/00* (2006.01)
(Continued)

(52) U.S. Cl.
CPC ........ *G06V 20/70* (2022.01); *A61B 1/000094* (2022.02); *A61B 1/000096* (2022.02);
(Continued)

(58) Field of Classification Search
None
See application file for complete search history.

(56) References Cited

U.S. PATENT DOCUMENTS 8,443,279 B1    5/2013  Hameed
2012/0209123 A1  8/2012  King
(Continued)

OTHER PUBLICATIONS

Baumhauer (Navigation in Endoscopic Soft Tissue Surgery Perspectives and Limitations, 2008) (Year: 2008).*
(Continued)

*Primary Examiner* — Kyle Zhai

(57) ABSTRACT

A controller (522) for live annotation of interventional imagery includes a memory (52220) that stores software instructions and a processor (52210) that executes the software instructions. When executed by the processor (52210), the software instructions cause the controller (522) to implement a process that includes receiving (S210) interventional imagery during an intraoperative intervention and automatically analyzing (S220) the interventional imagery for detectable features. The process executed when the processor (52210) executes the software instructions also includes detecting (S230) a detectable feature and determining (S240) at add an annotation to the interventional imagery for the detectable feature. The processor further includes identifying (S250) a location for the annotation as an identified location in the interventional imagery and adding (S260) the annotation to the interventional imagery at the identified location to correspond to the detectable feature. During the intraoperative intervention, a video is output (S270) as video
(Continued)

output based on interventional imagery and the annotation, including the annotation overlaid on the interventional imagery at the identified location.

20 Claims, 8 Drawing Sheets

(51) Int. Cl.
| | |
|---|---|
| G06T 7/00 | (2017.01) |
| G06T 7/13 | (2017.01) |
| G06T 7/246 | (2017.01) |
| G06T 7/30 | (2017.01) |
| G06T 7/73 | (2017.01) |
| G06T 11/00 | (2006.01) |
| G06V 10/44 | (2022.01) |
| G06V 10/764 | (2022.01) |

(52) U.S. Cl.
CPC .......... *A61B 1/0005* (2013.01); *G06T 7/0012* (2013.01); *G06T 7/13* (2017.01); *G06T 7/246* (2017.01); *G06T 7/30* (2017.01); *G06T 7/73* (2017.01); *G06T 11/00* (2013.01); *G06V 10/44* (2022.01); *G06V 10/764* (2022.01); *G06T 2207/10016* (2013.01); *G06T 2207/10068* (2013.01); *G06T 2207/20081* (2013.01); *G06T 2207/30064* (2013.01); *G06T 2207/30096* (2013.01); *G06V 2201/031* (2022.01); *G06V 2201/034* (2022.01)

(56) References Cited

U.S. PATENT DOCUMENTS

| | | | | |
|---|---|---|---|---|
| 2013/0038707 | A1* | 2/2013 | Cunningham | ......... H04N 7/183 |
| | | | | 382/131 |
| 2016/0210411 | A1 | 7/2016 | Mentis | |
| 2018/0325604 | A1* | 11/2018 | Atarot | .................. A61B 5/7475 |
| 2019/0069957 | A1 | 3/2019 | Barral | |
| 2019/0201116 | A1* | 7/2019 | Shelton, IV | ........... G16H 30/40 |
| 2019/0205625 | A1* | 7/2019 | Luo | ......... G06N 3/088 |
| 2020/0327733 | A1* | 10/2020 | Mueller | ............. G06F 3/04845 |
| 2020/0349365 | A1* | 11/2020 | Behrendt | ............... G06V 20/64 |

OTHER PUBLICATIONS

Wen et al. (Image-guided video-assisted thoracoscopic small lung tumor resection using near-infrared marking, Surgical Endoscopy, 2018) (Year: 2018).*
International Search Report and Written Opinion Dated Jan. 12, 2021 for International Application No. PCT/EP2020/075422 Filed Sep. 11, 2020.
Liu, et al: "Augmented reality and cone beam CT guidance for transoral robotic surgery", Journal of Robotic Surgery, Springer-Verlag, vol. 9, No. 3, Sep. 1, 2015.
Jin, et al: "Tool Detection and Operative Skill Assessment in Surgical Videos Using Region-Based Convolutional Neural Networks", 2018 IEEE Winter Conference on Applications of Computer Vision, Mar. 12, 2018.
Thienphrapa, et al: "Interactive Endoscopy: A Next-Generation, Streamlined User Interface for Lung Surgery Navigation", Oct. 10, 2019, 12th European Conference on Computer Vision.
Bernhardt, et al: "The status of augmented reality in laparoscopic surgery as of 2016", Medical Image Analysis, vol. 37, Apr. 1, 2017.
Leibetseder, et al: "Endometriosis Annotation in Endoscopic Videos", 017 IEEE Int Synp. Multimedia, pp. 364-365.
Mori, et al: "Automated Anatomical Labeling of the Bronchial Branch and Its Application to the Virtual Bronchoscopy System", IEEE Trans. Med. Imag., 19(2) Feb. 2000, pp. 103-114.

* cited by examiner

INTERACTIVE ENDOSCOPY FOR INTRAOPERATIVE VIRTUAL ANNOTATION IN VATS AND MINIMALLY INVASIVE SURGERY

CROSS REFERENCE TO RELATED APPLICATIONS

This application is the U.S. National Phase application under 35 U.S.C. § 371 of International Application No. PCT/EP2020/075422 filed Sep. 11, 2020, which claims the benefit of U.S. Provisional Patent Application No. 62/899,365 filed Sep. 12, 2019. These applications are hereby incorporated by reference herein.

BACKGROUND

An interventional medical procedure is an invasive procedure involving entry into the body of a patient. Surgery is an example of an interventional medical procedure, and is the preferred treatment for early stage lung cancer tumors. Also, endoscopy is increasingly used in different stages of lung cancer surgery. For lung cancer surgery, a basic precursor to resecting (removing) tumors is a "surgical exploration" stage, in which medical clinicians, such as surgeons, examine the lung tissue to mentally relate anatomical knowledge and preoperative imaging such as computed tomography (CT) to live endoscopic (e.g., thoracoscopic) video of the lung tissue. The surgical exploration stage helps ensure clinicians can resect the entirety of the lung cancer tumors in the resection stage, while avoiding resecting healthy lung tissue that could otherwise result in compromised lung function. Surgical exploration with a thoracoscope typically provides familiarity with lung tissue that cannot be obtained from preoperative imaging such as CT since preoperative imaging primarily shows differences in the attenuation of lung tissue to highlight anatomical landmarks. In surgical exploration, clinicians view the lung tissue through the thoracoscope while manipulating the lung tissue with instruments, so as to identify anatomical landmarks to facilitate resection. Specifically, during surgical exploration, clinicians attempt to identify known anatomical landmarks such as blood vessels and airways in the proximity of the lung cancer tumors in order to orient the anatomy properly to locate the lung cancer tumors and in order to avoid damaging the blood vessels and airways during resection.

The most invasive form of lung cancer surgery is open surgery, where the chest is split open to expose a large portion of the lung. In open surgery, surgical tools such as scalpels, electrocautery knives and sutures are inserted through a large opening in the thorax and used to resect the lung cancer tumors. In the past, lung cancer tumors were large enough to be sensed by touch, so clinicians could find lung cancer tumors that were invisible to the eye. The open surgery techniques allow physical access for palpation to sense the tumors by touch.

In recent years, both detection of embedded lung cancer tumors and techniques for surgically resecting lung cancer tumors have improved. For example, lung cancer screening programs now tend to identify early-stage tumor nodules that are small and difficult to discern. Additionally, a minimally invasive technique for resecting lung cancer tumors called video-assisted thoracoscopic surgery (VATS) has emerged as an alternative to open surgery.

Locating and resecting lung cancer tumors with safe margins while sparing healthy lung tissue is still an important aspect of success with VATS. In VATS, a small camera is inserted into the chest cavity through a small port (i.e. a small hole or incision) and the surgical instruments are inserted through the same port or other small ports. The entire surgical resection is performed using the camera view.

FIG. 1 illustrates a conventional VATS implementation for lung resection. In FIG. 1, a thoracoscope may be inserted through the rib cage of a patient P as one of the instruments. Vision that is otherwise occluded can be restored via the thoracoscope. In FIG. 1, instrument #1 and instrument #2 are separately inserted into the patient P via two separate small incisions to perform the resection. In recent years, robotic surgery has emerged as a minimally invasive approach similar to and competitive with VATS.

Nevertheless, three major challenges are still encountered in lung cancer surgery. First, well before surgery, the location of the lung cancer tumors may be determined based on a pre-operative CT scan with the lung fully inflated. So, when the lung is collapsed during subsequent surgery, the three-dimensional (3D) orientation of the lung and locations of the lung cancer tumors will not match the images from the pre-operative CT scan used for planning Second, the lung is complex with many blood vessels and airways that have to be carefully dissected and addressed before the lung cancer tumors and any feeding airways or vessels are removed. Third, since small, non-palpable lung cancer tumors are difficult to identify and locate, especially using VATS or robotic surgery, extra healthy lung tissue may still be removed during a procedure to prevent the possibility of leaving behind tissue of the lung cancer tumors.

To overcome these challenges, ways of improving the surgical workflow have been investigated to better guide resection of lung cancer tumors. The surgical exploration involved in VATS is time consuming, uncertain and unquantifiable, making many aspects of the procedure difficult to reproduce. Additionally, the interactive endoscopy for intraoperative virtual annotation in VATS and minimally invasive surgery described herein addresses these challenges.

SUMMARY

According to an aspect of the present disclosure, a controller for live annotation of interventional imagery includes a memory that stores software instructions and a processor that executes the software instructions. When executed by the processor, the software instructions cause the controller to implement a process that includes receiving interventional imagery during an intraoperative intervention and automatically analyzing the interventional imagery for detectable features. The process executed when the processor executes the software instructions also includes detecting a detectable feature and determining to add an annotation to the interventional imagery for the detectable feature. The process executed when the processor executes the software instructions further includes identifying a location for the annotation as an identified location in the interventional imagery and adding the annotation to the interventional imagery at the identified location to correspond to the detectable feature. During the intraoperative intervention, a video is output as video output based on the interventional imagery and the annotation, including the annotation overlaid on the interventional imagery at the identified location.

According to another aspect of the present disclosure, a system for live annotation of interventional imagery includes an electronic display and a controller. The electronic display displays the interventional imagery. The controller includes a memory that stores software instructions and a processor that executes the software instructions.

When executed by the processor, the software instructions cause the controller to implement a process that includes receiving interventional imagery and automatically analyzing the interventional imagery for detectable features. The process executed when the processor executes the software instructions also includes detecting a detectable feature and determining to add an annotation to the interventional imagery for the detectable feature. The process executed when the processor executes the software instructions further includes identifying a location for the annotation as an identified location in the interventional imagery and adding the annotation to the intervention al imagery at the identified location to correspond to the detectable feature. During the intraoperative intervention, a video is output as video output on the electronic display based on the interventional imagery and the annotation, including the annotation overlaid on the interventional imagery at the identified location.

According to still another aspect of the present disclosure, a method for live annotation of interventional imagery includes receiving interventional imagery during a video assisted thoracoscopic surgery for lung tumor resection from a thoracoscope that produces the interventional imagery as a view inside a chest. The method also includes automatically analyzing, by a processor executing software instructions from a memory, the intervention al imagery for detectable features. The method further includes detecting a detectable feature and determining to add an annotation to the interventional imagery for the detectable feature. The method moreover includes identifying a location for the annotation as an identified location in the interventional imagery and adding the annotation to the interventional imagery at the identified location to correspond to the detectable feature. During the video assisted thoracoscopic surgery, a video is output as video output based on the interventional imagery and the annotation, including the annotation overlaid on the interventional imagery at the identified location.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
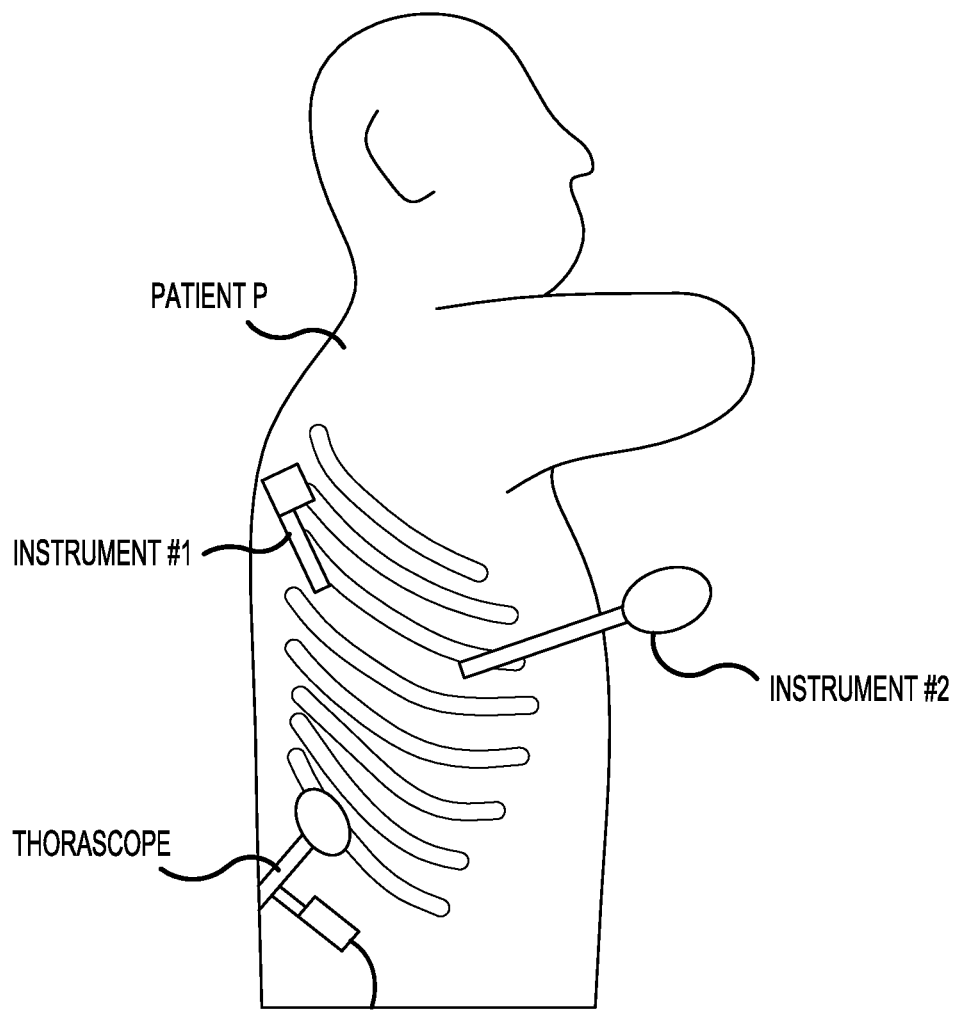
FIG. 1 illustrates a conventional video-assisted thoracoscopic surgery (VATS) implementation for lung resection.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a", "an" and "the" are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Interactive endoscopy for intraoperative virtual annotation in VATS and minimally invasive surgery as described herein provides an interactive annotation system for interactively annotating live video during surgery, which may be viewed during the interventional medical procedure. The interactive endoscopy further supplies informative annotations to assist personnel involved in medical interventions with annotating persistent features, anatomical or otherwise, with tracking the annotated persistent features via the annotations when found, and with noting tasks already performed.

FIGS. 2A to 2F illustrate methods for intraoperative virtual annotation in VATS and minimally invasive surgery, in accordance with various representative embodiments. Generally, the methods are to be performed during an interventional medical procedure using interactive endoscopy, for example, during which a thoracoscope and one or more surgical instruments are inserted in a patient. While examining tissue during the interventional medical procedure, the clinician views a display of interventional imagery (e.g., endoscopic imagery) that provides information such as anatomical features of interest and/or surgical events. The intervention al imagery may be video, for example, as provided by an endoscopic camera during VATS. According to the various embodiments, all or a portion of this information may be annotated on the display using the interactive annotation system, for example, by overlaying a virtual annotation on the interventional image to visualize the surgical field. The annotation may be placed in a position identified by the clinician or by the interactive annotation system based on machine learning applied to previous instantiations. The position at which the annotation is placed should make contextual sense, such as placing an annotation for a vessel where the vessel appears in the interventional imagery.

Additionally, the clinician may provide one or more instructions to trigger the overall annotation workflow or individual aspects of the annotation workflow. The clinician proceeds with the interventional medical procedure, adding annotations as desired. When the clinician identifies a feature or event to annotate, the clinician designates the feature or event to a software control system of the interactive annotation system, which assists in determining where and how to apply the annotation. In additional embodiments, the software control system may apply image processing algorithms to adjust the position and orientation of the annotation with respect to corresponding image locations as the tissue and/or endoscope move around.

Figure 2A:
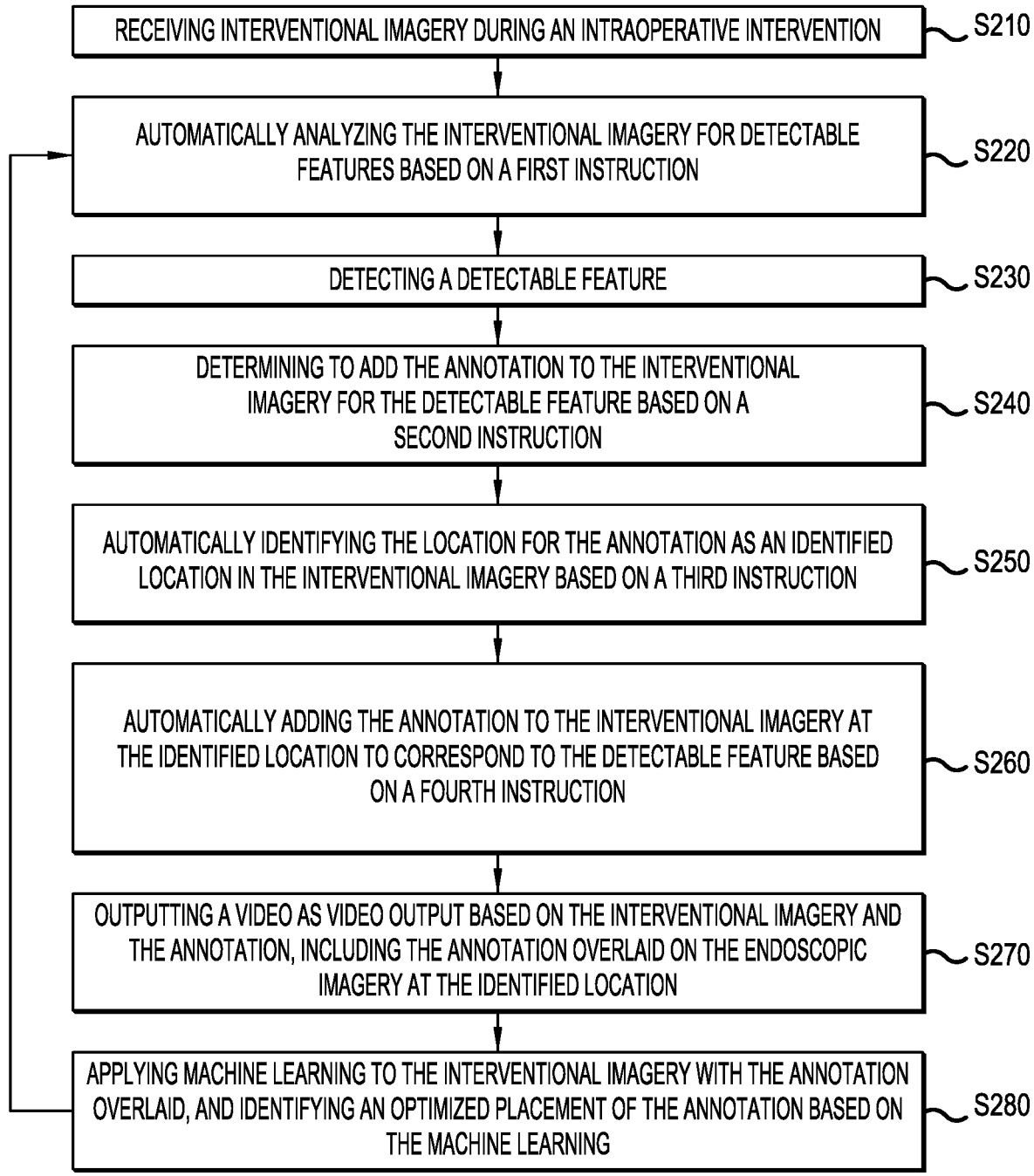
FIG. 2A illustrates a method for intraoperative virtual annotation in VATS and minimally invasive surgery, in accordance with a representative embodiment.

FIG. 2A illustrates a method for intraoperative virtual annotation in VATS and minimally invasive surgery, in accordance with a representative embodiment. The method of FIG. 2A may be implemented, for example, using controller 522 in a system 500 for interactive endoscopy of FIG. 5B, described below.

Referring to FIG. 2A, interventional imagery is received at S210 during an intraoperative intervention. The interventional imagery is captured using an imaging device such as an endoscopic camera on an endoscope for providing endoscopic imagery. For example, the endoscopic imagery may be video captured during an interventional medical procedure using the endoscope. Another example of an imaging device is a small camera positioned to be focused on particular parts of anatomy or tools during spine surgery or like procedures, in which case the interventional imagery is camera imagery such as video of the anatomy or tools. The interventional imagery may be obtained from outside of the patient or, in the case of endoscopic imagery, from inside the patient.

At S220, the interventional imagery is automatically analyzed for detectable features in response to a first instruction. The detectable features may include anatomical structures of patient anatomy and/or interventional tools used during the interventional medical procedure, for example. The analysis for detectable features at S220 may be performed using one or more video analysis algorithms, such as algorithms for detecting and tracking low-level features in an image (e.g., a video frame). For example, a first video analysis algorithm for detecting and tracking the low-level features may include a scale invariant feature transform (SIFT) algorithm, a speeded up robust features (SURF) algorithm, an optical flow algorithm, or a learned features algorithm. A second video analysis algorithm may be used to recognize and classify anatomical structures of interest from the extracted low-level features. A third video analysis algorithm may be used to compute tissue deformation such as rotation about any of three axes or linear translation in any of the directions of the three axes, where the three axes are set relative to a fixed object or location.

Automation of functional features described herein may be implemented based on machine learning such as deep learning algorithms. Machine learning may be implemented centrally for multiple different individual systems such as the system 500 of FIG. 5A, and the machine learning may be performed in a cloud-based processing system such as at a data center. Alternatively, the machine learning may be implemented centrally at a dedicated central computer system, such as for multiple different individual systems that are geographically dispersed but which have a relationship to the entity that provides the dedicated central computer system.

Instantiations of interventional imagery may be subject to machine learning to identify patterns and correlations, and the results of machine learning may be used to optimize aspects of the teachings herein such as analysis for detectable features at S220. Additionally, the interactive annotation system may be provided with setting information before an interventional medical procedure so as to assist the automation, such as by helping reduce processing demands. For example, setting information may be a type of medical intervention such as lung resection, so that the interactive annotation system analyzing the endoscopic imagery knows to look for types of anatomical features typically found in lungs. Alternatively, the interactive annotation system may automatically recognize context such as the environment of a lung, so as to narrow analysis for detectable features to those ordinarily found in or around a lung.

At S230, a detectable feature is detected in the interventional imagery. Insofar as a detectable feature may be an anatomical structure or a tool, one or more image recognition algorithms may be applied to detect the detectable feature or multiple detectable features. A tool detected as a detectable feature may be a forceps, sutures, staples fixed to anatomy, or other implantable devices, for example. The detection of a detectable feature at S230 may be based on recognizing one or more of shape, color, relative placement and/or other characteristics of the detectable feature.

At S240, it is determined that an annotation for the detectable feature is to be added to the interventional imagery in response to a second instruction. The second instruction received at S240 may reflect an affirmative determination to add an annotation for a detectable feature detected at 230, and may be received as the result of a prompt such as highlighting the detectable feature or an outline of the detectable feature on the screen after S230 and before S240. At S250, a location for the annotation is automatically identified in the interventional imagery in response to a third instruction. The identification of location at S250 may include identifying distance and directional placement relative to the corresponding detected feature and may take into consideration the context of where the detected feature is relative to the tumor, relative to other anatomical features, and/or relative to other tools in the interventional imagery. At S260, the annotation is automatically added to the interventional imagery at the identified location to correspond to the detectable feature in response to a fourth instruction. The fourth instruction received at S260 may reflect a confirmation that the identified location is acceptable and of the determination to add the annotation at S240. The first, second, third and fourth instructions may be software instructions, for example, provided by the controller 522, automatically and/or in response to input by the clinician.

At S270, a video is output including the interventional imagery and the annotation overlaid on the interventional imagery at the identified location. Overlaying of annotations onto endoscopic imagery may be performed using image overlay functions such as those contained in the open source software library OpenCV, for example.

In an embodiment, although not shown, the features from S210 to S270 may be performed in a loop so that even as video output is output at S270, the interventional imagery is being received and analyzed continually at S210 and S220. Based on the features from S210 to S270, the interactions between clinicians involved in the interventional medical procedure and the interactive annotation system may include receiving any of the various instructions, and performing corresponding functions based on the instructions. In this way, the clinicians involved in the interventional medical procedure can interactively control annotations on the interventional imagery in a way that is immediately useful. Additionally, the features from S210 to S270 may be implemented by an interactive annotation system that is provided entirely in a space in which the interventional medical procedure takes place, and in a continuous uninterrupted timeframe between when the interventional medical procedure starts by initially inserting medical equipment (e.g., a thoracoscope) into the patient and when the intervention al medical procedure ends when the medical equipment is removed from the patient. Alternatively, the features from S210 to S270 may start when an interactive annotation system is affirmatively started such as by a command, to when the interactive annotation system is affirmatively shut off such as by an instruction from a clinician involved in the interventional medical procedure.

At S280, machine learning is applied to the interventional imagery with the annotation overlaid, and an optimized placement of the annotation is identified based on the machine learning. The machine learning used in S280 may be for optimizing annotation placement, though the machine learning may also be used for improving functionality of the interactive annotation system, for understanding tasks and image content in interventional medical procedures, and/or for adapting user interfaces too. The process from S220 to S280 may be performed in a loop for multiple medical interventions.

The functionality specific to S280 reflects the actual placement of the annotation. The actual details of the annotation and placement may be pooled with actual details of other instantiations so as to identify averages such as distance from the related detectable feature and whether the annotation interferes with other features of the interventional imagery in a way that may be problematic. As an example, optimized annotation placements may be learned by applying machine learnings to obtain quantitative metrics of existing pairs of anatomical features and virtual labels. For example, quantitative metrics may include distances between the anatomical features and virtual labels. As another example, quantitative metrics may include areas or volumes of certain types of virtual labels, or between certain types of anatomical features and virtual labels.

The machine learning applied at S280 is only one example of machine learning that can be applied according to the teachings herein. Examples of machine learning for functionality of the interactive annotation system also include feature detection such as at S220 and S230. Feature detection may include learning how and where to find detectable patterns and anatomical features, such as by studying multiple instantiations of previous endoscopy imagery and identifying commonalities related to how and where users set annotations for particular types of detectable features. Feature detection may also include learning patterns of when users place annotations in the context of particular types of medical interventions.

Machine learning for understanding tasks and image content in interventional medical procedures may be used for many purposes. For example, feature detection may be used to learn to find clinically relevant anatomical features and landmarks such as at S220 and S230. Machine learning may also be used to learn what annotations are used for a given interventional medical procedure, and when/where these annotations are placed such as at S250. Machine learning may also be used to learn what annotations correspond to a surgical event or action, the timing and order of sequences of annotation placement, and patterns of surgical workflow reflecting the thought processes of personnel involved in medical interventions. Machine learning may also be used to learn when annotations disappear from view, such as when annotations for an anatomical structure disappear when the anatomical structure is part of an organ that is flipped or otherwise rotated. Machine learning may also be used to identify relationships between similar annotations used in different interventional medical procedures.

Examples of machine learning for adapting user interfaces may be used to identify which annotations should be used for particular anatomy. Machine learning for adapting user interfaces may also be used to learn appropriate sizes and orientations for annotations, and even details such as size and font for textual annotations. Machine learning for user interfaces may also be applied to learn numbers of annotations to be used, such as a maximum number or optimal number. Machine learning for user interfaces may also identify patterns of when particular annotations or types of annotations are explicitly removed, such as when personnel involved in the interventional medical procedure determine the annotations are no longer useful. Machine learning may also be used to identify user preferences so that options for annotations can be customized for any particular user.

The machine learning may be used in a form of feedback loop, where aspects of annotations in one interventional medical procedure reflect optimization from machine learning in previous interventional medical procedures. That is, annotations in one interventional medical procedure may be based on machine learning applied to at least one previous instantiation of live annotation. The interventional imagery of the one interventional medical procedure may, in turn, be studied and incorporated into the machine learning so as to be applied in optimization for later interventional medical procedures.

As described above, in the method of FIG. 2A, a detectable feature may be detected based on automatically analyzing the interventional imagery. A virtual annotation is placed in the interventional imagery to correspond to the detectable feature, and the annotated interventional imagery is output as annotated video including the interventional imagery and the annotation. The annotation may serve as a form of augmented reality. For example, the annotated interventional imagery may be used as a roadmap so that the clinician does not have to repeatedly detect and identify the same detectable features. Of course, annotations are not limited to detectable features from anatomy, as the annotated interventional imagery is also used to identify tools and to provide a checklist of completed tasks and other information during a surgery, for example.

As described above, the interactive annotation system may be used to control interactive endoscopy for intraoperative virtual annotations. The interactive annotation system provides functional features including at least analysis of input to live surgical video for detecting detectable features, acceptance of dynamic command inputs to add virtual annotations (e.g., labels) to the live surgical video, determination of location(s) in the video where the annotations are to be added, and production of an output video that contains the original surgical video with overlaid annotations.

Figure 2B:
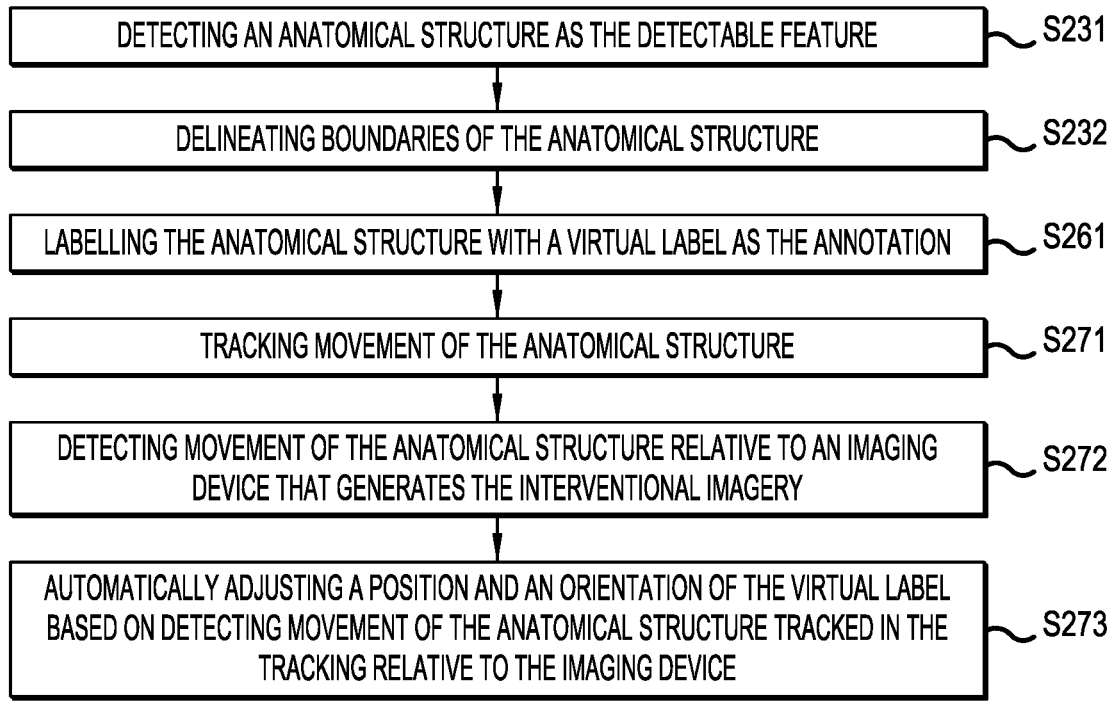
FIG. 2B illustrates another method for intraoperative virtual annotation in VATS and minimally invasive surgery, in accordance with a representative embodiment.

FIG. 2B illustrates another method for intraoperative virtual annotation in VATS and minimally invasive surgery, in accordance with a representative embodiment. The method of FIG. 2B may be supplemental to the method of FIG. 2A where appropriate, although individual features of the method of FIG. 2B may replace individual features of the method of FIG. 2A where noted or where otherwise appropriate.

Referring to FIG. 2B, an anatomical structure is detected at S231 as the detectable feature, in which case S231 replaces S230 from FIG. 2A as an example of the type of detectable feature to be detected. At S232, boundaries of the detected anatomical structure are delineated. The boundaries may be delineated, for example, by graphically identifying and outlining the boundaries such as by highlighting the color or another aspect of the appearance of the anatomical structure at the boundaries.

At S261, the anatomical structure is labeled with a virtual label as the annotation. Labeling the anatomical structure at S261 in FIG. 2B is an example of the automatic addition of the annotation at S260 in FIG. 2A. The virtual label may include a marker with text, or numbers and/or icons within a shape such as a predetermined outline corresponding to an anatomical structure, for example. Labels and other annotations may range in semantic sophistication. For example, annotations may note the time, identify a vessel, or outline a tumor. Additionally, annotation instructions can be provided by touchscreen, voice, or automatically. The labelling at S261 may be performed after features from FIG. 2A such as determining to add the annotation at S240 and identifying the location for the annotation at S250. That is, features of FIG. 2A that are now described for the embodiment of FIG. 2B may still be included in the embodiment of FIG. 2B when appropriate.

Examples of annotatable information that can be included in an annotation, such as a virtual label, include tags for various anatomical features such as lung fissures, tumors, vessels, airways, and other organs. A virtual label may include multiple checklist items, in which case examples of annotatable information include surgical events such as incision, stapling, excision, grasping, flipping, and stretching. Other examples of annotatable information include perioperative information such as elapsed time and forces rendered. Detailed information may be provided as the annotatable information, such as detailed information assessed based on intraoperative information, and sometimes even combined with external reference data which may include various forms of physiological data, models, and imaging. Postoperative information such as staple lines or the exact tumor location, which can serve as input to future learning algorithms, may also be provided as the annotatable information. Most annotatable information described herein can be used as live feedback in a form of roadmaps for the medical personnel involved in the interventional medical procedure.

Movement of the anatomical structure is tracked at S271, which may occur after the video output is output at S270 in the method of FIG. 2A. For example, movement of the anatomical structure may be tracked when the anatomical structure is rotated or translated in horizontal and/or vertical directions. The anatomical structure may also move relative to a viewpoint of an imaging device such as an endoscopic camera when the imaging device moves. At S272, movement of the anatomical structure is detected relative to the imagining device such as the endoscopic camera that generates the interventional imagery. The movement of the anatomical structure inherently reflects the usefulness of the corresponding virtual label, so movement of the anatomical structure may be tracked to be sure the virtual label moves with the anatomical structure.

At S273, a position and an orientation of the virtual label is automatically adjusted based on detecting the movement of the anatomical structure tracked in the tracking relative to the endoscope. The adjusting at S273 may be based on measuring the deformation of the corresponding anatomical structure, such as rotation about any of three axes or linear translation in directions along any of the three axes.

Figure 2C:
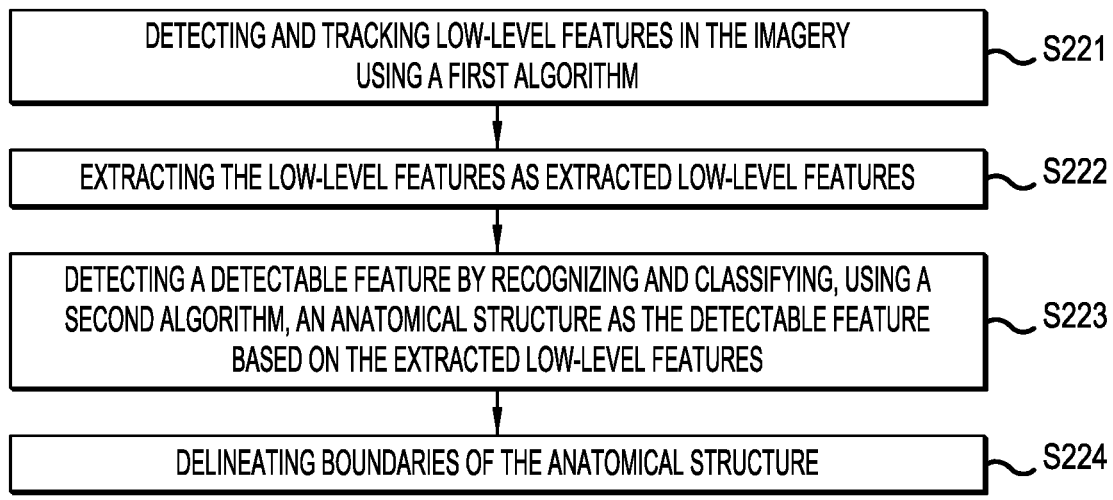
FIG. 2C illustrates another method for intraoperative virtual annotation in VATS and minimally invasive surgery, in accordance with a representative embodiment.

FIG. 2C illustrates another method for intraoperative virtual annotation in VATS and minimally invasive surgery, in accordance with a representative embodiment. The method of FIG. 2C may be supplemental to the method of FIG. 2A where appropriate, although individual features of the method of FIG. 2C may replace individual features of the method of FIG. 2A where noted or where otherwise appropriate.

Referring to FIG. 2C, low-level features in the interventional imagery are detected and tracked using a first algorithm at S221, which may be performed as part of the analysis at S220 in FIG. 2A. Low-level features include features that form a pattern that is relatively unique in the details of the interventional imagery in order to be interpretable as an anatomical structure or a tool. The low-level features include patterns that may not be recognizable to a human, may not be observable to a human, or may otherwise be undetectable by a human by the naked eye. As noted previously, examples of algorithms for detecting and tracking low-level features in an image such as a video frame include a scale invariant feature transform (SIFT) algorithm, a speeded up robust features (SURF) algorithm, an optical flow algorithm, or a learned features algorithm.

At S222, the method of FIG. 2C includes extracting the low-level features as extracted low-level features. S222 may also be performed as part of the analysis at S220 in FIG. 2A.

The method of FIG. 2C continues at S223 with detecting a detectable feature by recognizing and classifying, using a second algorithm, an anatomical structure as the detectable feature in the endoscopic imagery based on the extracted low-level features. S223 may be performed as part of the detecting at S230 in FIG. 2A. A second algorithm may include features such as comparing low-level features detected by the first algorithm with known characteristics of known anatomical features, such as by color, size, shape, proximity to other known characteristics. Both the low-level features and the characteristics of known anatomical features may have patterns that do not have meaning to a human, are not observable to a human, or otherwise are not detectable by a human such as by the naked eye, but which are still recognizable and detectable by algorithms used in image processing. The second algorithm may rank possible matches by how closely they match characteristics of known anatomical features, and then select a top-ranked known anatomical feature. The top-ranked known anatomical feature for a low-level feature may then be classified as relevant or irrelevant, such as based on the type of medical intervention being performed. Alternatively, the classification may be for the type of known anatomical feature, such as bone or tissue, organ or airway, other type. The algorithm may then selectively prompt the personnel involved in the interventional medical procedure to annotate a recognized anatomical feature based on the type of known anatomical feature, as well as the relevance to the medical interventional procedure being performed.

At S224, the method of FIG. 2C may include delineating boundaries of the anatomical structure. Delineating at S224 may be performed by overlaying a solid line or broken line to mark the boundaries of the anatomical structure.

As described above, in FIG. 2C image analysis and feature detection may be performed using one or more algorithms for image analysis and feature classification. The process of FIG. 2C may be performed, for example, for each of multiple frames in endoscopic imagery. The image analysis and feature detection may be performed throughout an interventional medical procedure once endoscopic imagery is first generated, or once a specific command is received to start the image analysis and feature detection or to specifically add an annotation. That is, personnel involved in an interventional medical procedure may dynamically decide to annotate a feature during the interventional medical procedure, and the processing starting at S220 in FIG. 2A or S221 in FIG. 2C may start based on the personnel involved in the interventional medical procedure initiating the processes described herein.

Figure 2D:
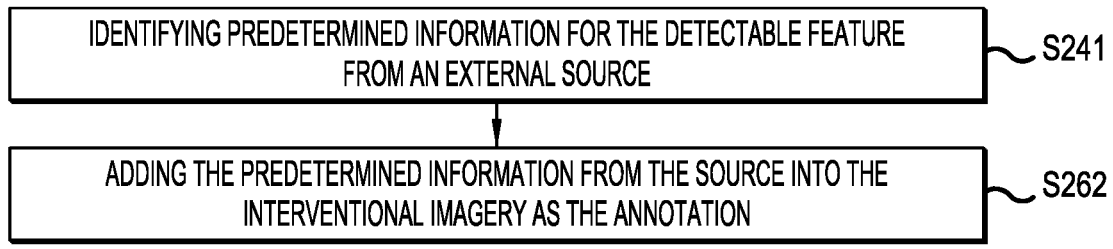
FIG. 2D illustrates another method for intraoperative virtual annotation in VATS and minimally invasive surgery, in accordance with a representative embodiment.

FIG. 2D illustrates another method for intraoperative virtual annotation in VATS and minimally invasive surgery, in accordance with a representative embodiment. The method of FIG. 2D may be supplemental to the method of FIG. 2A where appropriate, although individual features of the method of FIG. 2D may replace individual features of the method of FIG. 2A where noted or where otherwise appropriate.

Referring to FIG. 2D, predetermined information for the detectable feature is identified from an external source at S241. For example, a label, icon, item of information or other predetermined information may be identified at S241 when it is determined to add an annotation at S240 in the process of FIG. 2A. At S262, the predetermined information from the external source is added into the interventional imagery as the annotation. For example, upon receiving the fourth instruction at S260, the predetermined information from the external source may be added to the interventional imagery as a form of annotation at S262 as a modification or supplement to the automatic adding of the annotation at S260 of FIG. 2A.

Figure 2E:
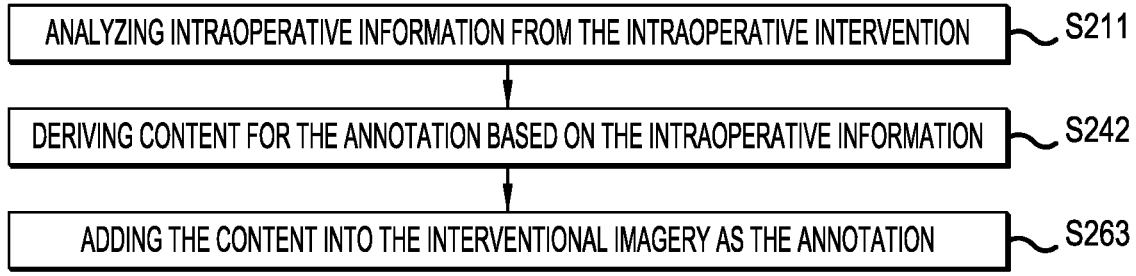
FIG. 2E illustrates another method for intraoperative virtual annotation in VATS and minimally invasive surgery, in accordance with a representative embodiment.

FIG. 2E illustrates another method for intraoperative virtual annotation in VATS and minimally invasive surgery, in accordance with a representative embodiment. The method of FIG. 2E may be supplemental to the method of FIG. 2A where appropriate, although individual features of the method of FIG. 2E may replace individual features of the method of FIG. 2A where noted or where otherwise appropriate.

Referring to FIG. 2E, intraoperative information from the intraoperative intervention is analyzed at S211. The intraoperative information may include details regarding the setting of the interventional medical procedure in which processes described herein are performed. For example, intraoperative information may include speech or gestures or specific inputs by the medical personnel involved in the interventional medical procedure. The intraoperative information may also include information output from medical equipment, such as monitors for heartbeat and pulse, and times when the information is output. The analysis at S211 may be for a specific predetermined type of intraoperative information or may be for multiple predetermined types of intraoperative information.

At S242, the content for the annotation is derived based on the intraoperative information being analyzed. For example, the annotation content may be derived from intraoperative information based on a conversation or sound in an operating room, as well as intraoperative information from imagery taken in an operating room, such as a camera, an endoscope or another mechanism for medical imaging. The annotation content may be derived from intraoperative information based on electronic signals from equipment, such as signals indicating a tool being turned on or off, lights being turned on or off or up or down, or a blood pressure monitor emitting an alarm as a patient's blood pressure exceeds an upper threshold or lower threshold. These are all examples of how content for an annotation can be derived in real time based on intraoperative information at S242 derived from the analyzing at S241. The annotation itself may then be placed as a note on the interventional imagery so as to be in the view of the medical personnel involved in the interventional medical procedure.

At S263, the process of FIG. 2E includes adding the content into the endoscopic imagery as the annotation. For example, upon receiving the fourth instruction at S260, the content derived from the intraoperative information may be added as a form of annotation at S263 as a modification or supplement to the automatic adding at S260 of FIG. 2A.

Figure 2F:
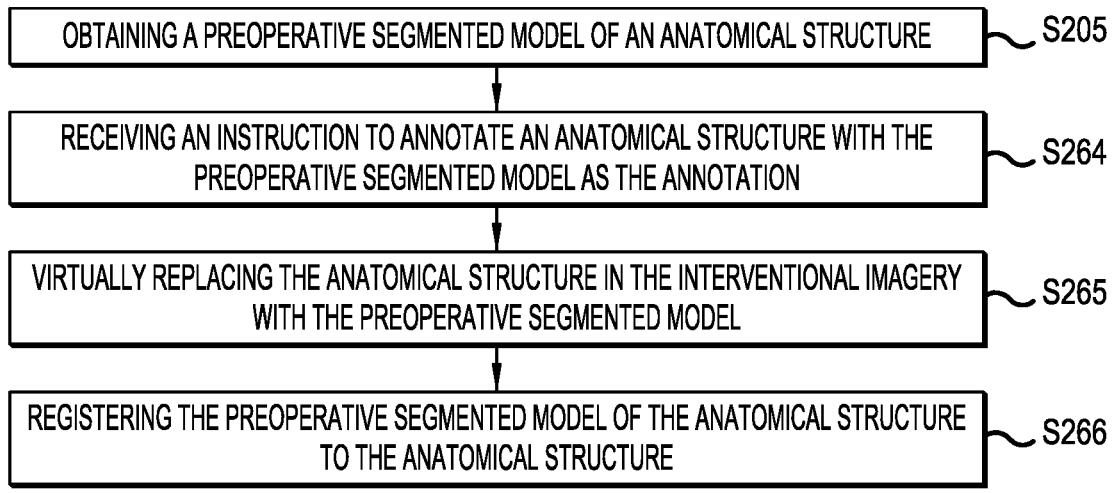
FIG. 2F illustrates another method for intraoperative virtual annotation in VATS and minimally invasive surgery, in accordance with a representative embodiment.

FIG. 2F illustrates another method for intraoperative virtual annotation in VATS and minimally invasive surgery, in accordance with a representative embodiment. The method of FIG. 2F may be supplemental to the method of FIG. 2A where appropriate, although individual features of the method of FIG. 2F may replace individual features of the method of FIG. 2A where noted or where otherwise appropriate.

Referring to FIG. 2F, a preoperative segmented model of an anatomical structure is obtained at S205. For example, the preoperative segmented model may be obtained from a preoperative computed tomography (CT) scan of an anatomical structure. The preoperative CT scan is used to generate a model which is then segmented.

At S264, an instruction to annotate an anatomical structure is received along with the preoperative segmented model as the annotation. That is, whatever anatomical structure is represented by the preoperative segmented model from S205 corresponds to the instruction at S264.

At S265, the anatomical structure in the endoscopic imagery is virtually replaced with the preoperative segmented model of the anatomical structure. That is, at S265 an instruction is received to replace the live interventional imagery of the anatomical structure with the preoperative segmented model of the anatomical structure obtained at S205.

At S266, the preoperative segmented model of the anatomical structure is registered to the anatomical structure. That is, at S266 the live interventional imagery of the anatomical structure is registered with the preoperative segmented model of the anatomical structure obtained at S205. As a result, an annotation automatically added at S260 involves registering and replacing the live interventional imagery of the anatomical structure with the preoperative segmented model of the anatomical structure obtained at S205. This form of annotation may assist the personnel involved in the interventional medical procedure in visualizing aspects of anatomy of a patient on a screen, so as to help improve focus. That is, as with most or all forms of annotations described herein, the annotations of FIG. 2F may be used as live feedback for the clinician involved in the interventional medical procedure, as assistance similar to a roadmap or navigation tool and/or as assistance similar to a sticky note.

Any two or more of the methods in FIGS. 2A-2F may be integrated together within the scope of the present disclosure. Additionally, the methods in FIGS. 2A-2F may include additional features, such as storing detected features that are identified and tracked from the intervention al imagery. Stored features may be used later such as, for example, if the endoscopic camera view moves to a significantly different area of an organ and then returns to the initial field of view so that the annotations such as virtual labels are automatically provided again. Some or all aspects of the methods and processes of the representative embodiments described above in connection with FIGS. 2A to 2F may be implemented by the system 500 of FIG. 5A, or even independently by the controller 522 of FIG. 5B executing software instructions.

Stored features and annotations may also be used in subsequent intervention al procedures, even on different days. For example, when one or more anatomical features are identified in a first interventional medical procedure and similar anatomical features are identified in a second interventional medical procedure, the similar features may be used to register the position and orientation of additional labels from the first interventional medical procedure automatically in the second interventional medical procedure. This results in less processing and quicker annotations for known features. For example, a tumor boundary may be defined in a first interventional medical procedure and a second interventional medical procedure, and an area and/or volume of the tumor may be quantified in each of the first interventional medical procedure and the second interventional medical procedure so that a difference between the areas can be computed.

Stored features and annotations may also be used for reporting purposes after an interventional medical procedure. For example, a number of features and the types of features can be saved to a patient electronic medical record. Alternatively, when the features are types of implants/tools/devices that are used, a count may be maintained for a purchasing system to re-stock these implants/tools/devices.

Figure 3:
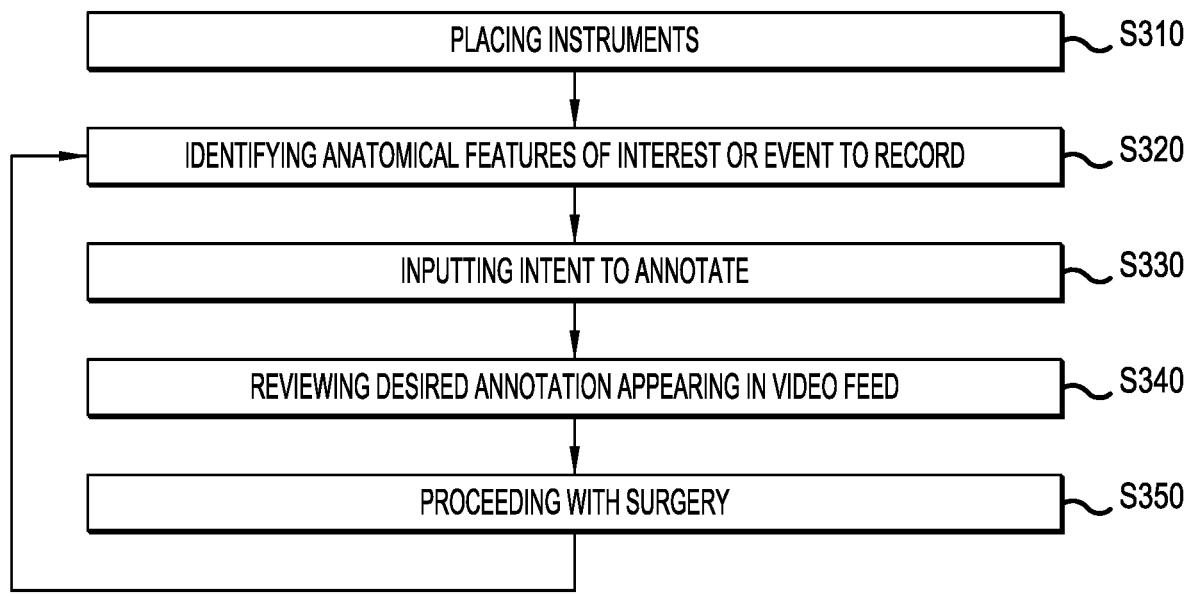
FIG. 3 illustrates another method for intraoperative virtual annotation in VATS and minimally invasive surgery, in accordance with a representative embodiment.

FIG. 3 illustrates another method of interactive endoscopy for intraoperative virtual annotation in VATS and minimally invasive surgery, in accordance with a representative embodiment. Some or all aspects of the methods and processes of the representative embodiment described above in connection with FIG. 3 may be implemented by the system 500 of FIG. 5A, or even independently by the controller 522 of FIG. 5B executing software instructions.

Referring to FIG. 3, at S310, instruments are placed in a medical interventional setting such as in an interventional medical procedure. The instruments are placed in or around the anatomy of the patient within the view of an imaging apparatus for the purposes of the explanations herein. Anatomical features of interest or an event to record is identified at S320. S320 is representative of triggers for the annotation processes described herein, in that identifying anatomical features of interest and/or an event to record for annotation are part of the process of ultimately annotating the interventional imagery.

At S330, an intent to annotate is input by the clinician via a touchscreen, keyboard, button, roller pad, mouse or other physical interface. The intent to annotate may also be input via an audible instruction or visual gesture detected by a speech recognition mechanism or video recognition mechanism implemented by a processor executing software instructions. At S340, a desired annotation is reviewed at it appears in a video feed. The reviewed annotation results from the intent inputted at S330, and may be an annotation overlaid onto or even visually integrated into the video feed at S340. The annotation may be the result of the various processing described with respect to embodiments from FIG. 2A to FIG. 2F. At S350, the clinician proceeds with surgery or another form of intervention in the interventional medical procedure for which the virtual annotations are provided. In an embodiment, the process from S320 to S350 may be performed in a loop during the interventional medical procedure.

Figure 4:
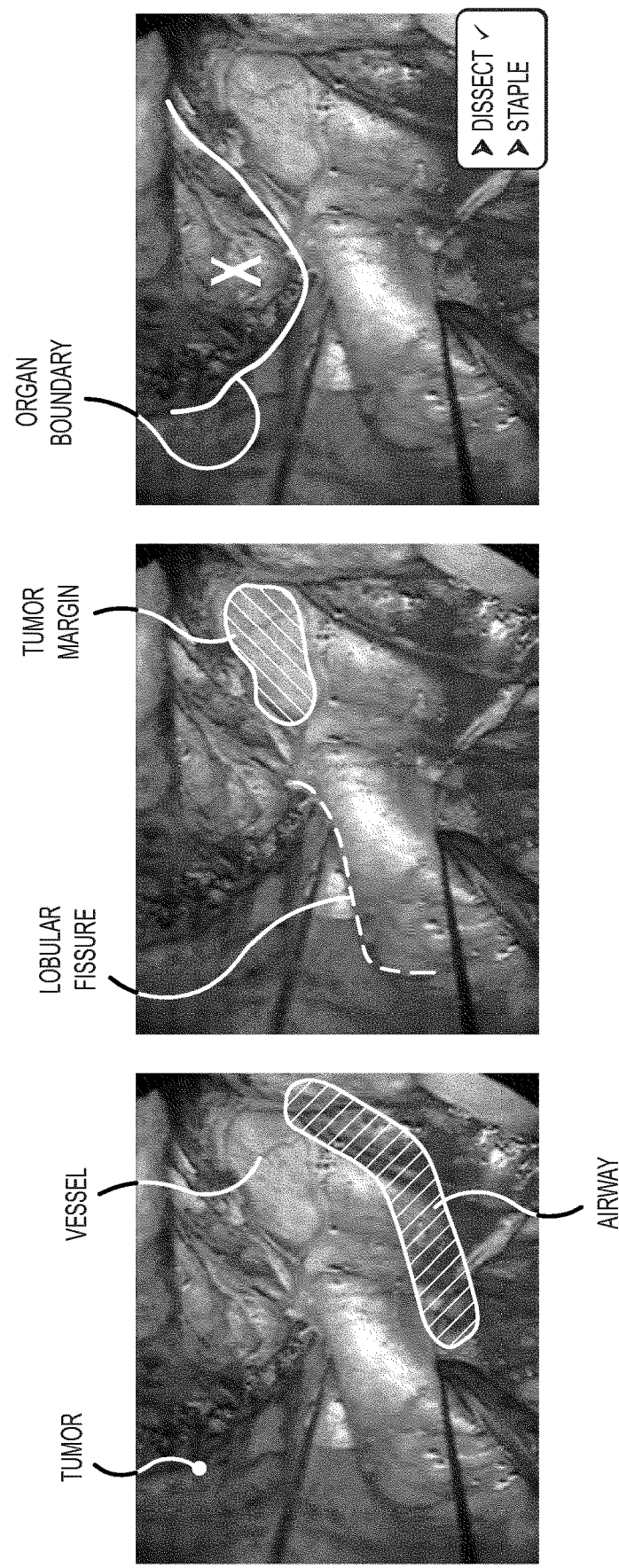
FIG. 4 illustrates three examples of virtual annotations for intraoperative virtual annotation in VATS and minimally invasive surgery, in accordance with a representative embodiment.

FIG. 4 illustrates three examples of virtual annotations of interactive endoscopy for intraoperative virtual annotation in VATS and minimally invasive surgery, in accordance with a representative embodiment.

Referring to FIG. 4, in a first example of annotations shown on the left, a tumor is labelled as "TUMOR," a vessel is labelled as "VESSEL," and an airway is labelled as "AIRWAY." In addition, the airway is overlaid with a virtual structure as an annotation to clearly designate the airway. In the depicted example, the labels are offset from the imagery of tissue, but this is not necessary and the labels may be overlaid onto imagery of tissue or onto interventional imagery in margins. In the second example of annotations, an anatomical surface is labelled as "LOBULAR FISSURE," and a tumor margin is labelled as "TUMOR MARGIN." Also, a boundary of the tumor margin is overlaid with a virtual structure to clearly designate the tumor and the tumor margin. In the first and second examples, the text labels may be replaced with simpler icons such as "A," "B," "C," "D" and "E" or numbers from "1" to "5". In the third example of annotations shown on the right, the annotations include a freehand curved outline and the label "X" overlaid on the imagery of tissue. The curved outline is also labelled with "ORGAN BOUNDARY," which is offset from the imagery of tissue. Additionally, a label with a checklist is overlaid on the imagery of the tissue on the lower right.

Accordingly, FIG. 4 illustrates multiple examples of how interventional imagery can be annotated. The various annotations may vary by size, type, location, color, text, shading, orientation, and more. Additionally, some annotations may be offered for use in certain types of medical interventions but not in others, or for particular individuals based on input from the individuals that is incorporated into machine learning.

Examples of types of annotations that may be provided as virtual annotations consistent with the present disclosure include markers, labels, differentiated colors, lines and curves, computer aided design (CAD) models, and drawings. Markers include dots, stars, squares, dashes, arrows, and other symbolic icons that convey position, direction, anatomical context, time, or other pertinent information. Labels may include text and other semantic representations that convey embedded information as tags. Differentiated colors may be used to delineate regions of tissue or may be used to represent other forms of information. Lines and curves may be used to indicate positions or boundaries of clinical interest and may be input via a touchscreen for example. CAD models may include segmented preoperative computed tomography (CT) images that represent anatomical structures such as tumors, vessels, airways, or other tissues of interest. Drawings may allow the personnel involved in the interventional medical procedure to sketch arbitrarily on the video screen and have the marking positions updated per the video content. Some examples of the aforementioned marker types are shown in FIG. 4. Additionally, markers or other forms of annotation may be variable, so as to convey transitions through space or time, or to convey transient information such as tool-to-tissue interaction.

In the embodiments of FIG. 4 and for other embodiments herein, locations and/or shapes of virtual annotations can be updated with each video frame, depending on image content. For example, a shaded region in a specific color such as green in the second example may disappear if the lung is flipped and the corresponding tissue is not in the view.

Figure 5A:
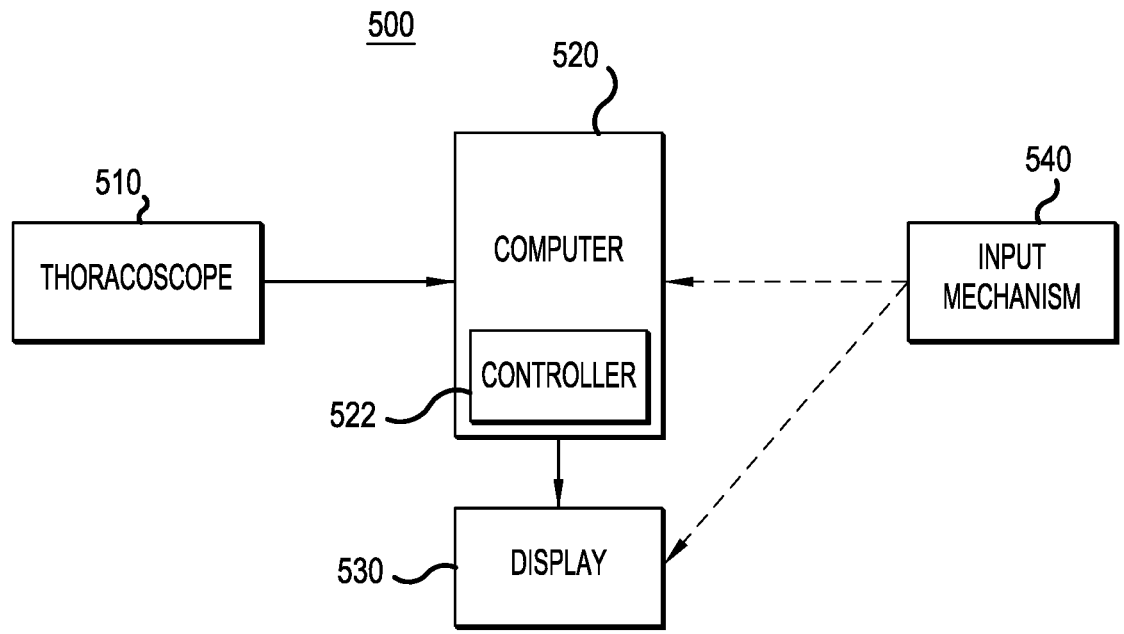
FIG. 5A illustrates a system for interactive endoscopy for intraoperative virtual annotation in VATS and minimally invasive surgery, in accordance with a representative embodiment.

FIG. 5A illustrates a system for interactive endoscopy for intraoperative virtual annotation in VATS and minimally invasive surgery, in accordance with a representative embodiment.

As shown in FIG. 5A, the system 500 includes a thoracoscope 510, a computer 520, a display 530, and an input mechanism 540. The computer 520 includes a controller 522. The system 500 is a simplified block diagram of what may otherwise be a much more complicated environment for implementing the teachings herein. The system 500 may include some or all components of an interactive annotation system described herein. The system 500 implements some or all aspects of the methods and processes of the representative embodiments in connection with FIGS. 2A to 3 as described herein.

The thoracoscope 510 is an example of an endoscope. A thoracoscope 510 is an elongated camera used typically for examination, biopsy and/or resection within the chest cavity (thoracic cavity). The thoracoscope 510 sends endoscopic imagery (e.g., video) to the computer 520 via a wired connection and/or via a wireless connection such as Bluetooth, for example.

The computer 520 includes at least the controller 522 but may include any or all elements of an electronic device such as in the computer system 600 of FIG. 6, explained below. For example, the computer 520 may include ports or other forms of communications interfaces to interface with the thoracoscope 510 and the display 530. The controller 522 includes at least a memory that stores software instructions and a processor that executes the software instructions to directly or indirectly implement some or all aspects of the various processes described herein.

The display 530 may be a video display that displays endoscopic imagery or other interventional imagery derived from the thoracoscope 510 and/or any other imaging equipment present in the environment where the interventional medical procedure takes place. The display 530 may be a monitor or television that displays video in color or black and white, and may also have an audio capability to output audio signals.

The input mechanism 540 may be or include a mouse, a keyboard, a touchpad, a tablet, a microphone, a video camera (for capturing, e.g., gestures) or any other item of equipment by which the clinician can input an instruction. The instructions input to the input mechanism 540 may be used in the process for annotating the endoscopic imagery or other intervention al imagery as described herein. As shown, the input mechanism 540 may communicate with the computer 520, but also may communicate with the display 530 such as when the input mechanism is a touchscreen on, in or otherwise connected to or with the display 530. The input mechanism 540 may communicate over wired or wireless connections, and as noted above, and may be part of or integrated with the display 530 and/or the computer 520.

The input mechanism 540 may be provided in different ways so that different methods can be selectively suited to specific contexts for various types of information and annotations. The input mechanism 540 may be or include a personal computer mouse and keyboard, so that the personal computer mouse is used to point at desired annotation locations such as a lung fissure visible on the lung surface or draw along a continuum of desired locations, and the keyboard is used to type in a text label as an annotation. The input mechanism 540 may be or include a touchscreen to perform tasks such as location selection and data input without a keyboard and mouse. External buttons mounted on an instrument and/or elsewhere may be used as the input mechanism 540 to recreate the functionality of a mouse in a location convenient to clinician(s) involved in the interventional medical procedure.

Image/video recognition software programs may be used as the input mechanism 540 in conjunction with a camera so as to recognize gestures. For example, in the example of image/video recognition software programs, movement of a surgical instrument in a particular pattern within the endoscopic view may activate annotation placement. Other examples of gestures that can be recognized by image/video recognition software programs include opening and closing a gripper such as twice in succession, rolling an item back and forth, or tapping gently against the tissue. Recognized gestures may be used to encode the type of annotation, or the type of annotation may be supplied through other means discussed herein. The input mechanism 540 may also be or include voice recognition software. In the example of voice recognition software, a voice command may activate placement, removal or changes in a virtual annotation, while simultaneously furnishing the type of annotation to be used. The input mechanism 540 may also recognize physical labeling of tissue such as with image/video recognition software programs. For example, an image/video recognition software program may recognize physical labelling indicating where to place a suture or a cautery mark on the tissue surface to identify a particular feature. As other examples of the input mechanism 540, virtual annotations may be automatically placed or suggested based on models, machine learning or deep learning, or other data driven methods. Examples of machine learning described herein may analyze video content to recognize features and actions. For example, using machine learning applied to previous instantiations, features labelled dynamically during a particular medical intervention can be analyzed and detected based on similar features that appear similar to those labeled previously are labeled automatically. As one more example of the input mechanism 540, partial or semi-automatic entry of a virtual annotation may trigger an "auto-completion" of the annotation. For example, auto-completion may be implemented when drawing a vessel onto an image causes a preoperative model of the vessel to be overlaid on the video, using the drawing as a registration guide.

Machine learning may be provided for the system 500 by a central system, for example, that receives instantiations of virtual annotations from the system 500 over the internet or other network, and that provisions the system 500 with results of machine learning over the internet or other network based on instantiations of virtual annotations from numerous systems including the system 500. For example, the machine learning may be performed in a cloud-based processing system such as at a data center. Alternatively, the machine learning may be implemented centrally at a dedicated central computer system, such as by an entity that has a relationship to the system 500.

Figure 5B:
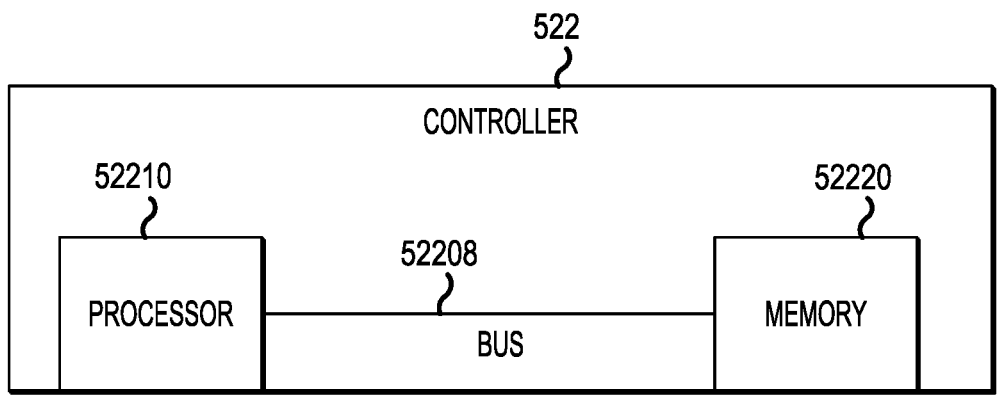
FIG. 5B illustrates a controller for interactive endoscopy for intraoperative virtual annotation in VATS and minimally invasive surgery, in accordance with a representative embodiment.

FIG. 5B illustrates a controller for interactive endoscopy for intraoperative virtual annotation in VATS and minimally invasive surgery, in accordance with a representative embodiment.

The controller 522 in FIG. 5B includes a processor 52210, a bus 52208 and a memory 52220. The controller 522 includes components for implementing some or all aspects of the methods and processes of the representative embodiments described above in connection with FIGS. 2A to 3. The processor 52210 is fully explained by the descriptions of a processor in the computer system 600 of FIG. 6 below. The processor 52210 executes software instructions to implement some or all aspects of the methods and processes of the representative embodiments described above in connection with FIGS. 2A to 3. The memory 52220 is fully explained by the descriptions of a memory in the computer system 600 of FIG. 6 below. The memory 52220 stores the software instructions executed by the processor 52210 to implement some or all aspects of the methods and processes described herein. The bus 52208 connects the processor 52210 and the memory 52220. The controller 522 is shown as a stand-alone element in FIG. 5B, and this illustrates that the controller 522 does not have to be provided as a part of the computer 520 in FIG. 5B. Rather, a controller 522 described herein may be provided as a stand-alone element to implement some or all aspects of methods described herein or may be integrated into a variety of devices such as an item of dedicated medical technology, a laptop computer or desktop computer, or a smartphone or tablet.

Figure 6:
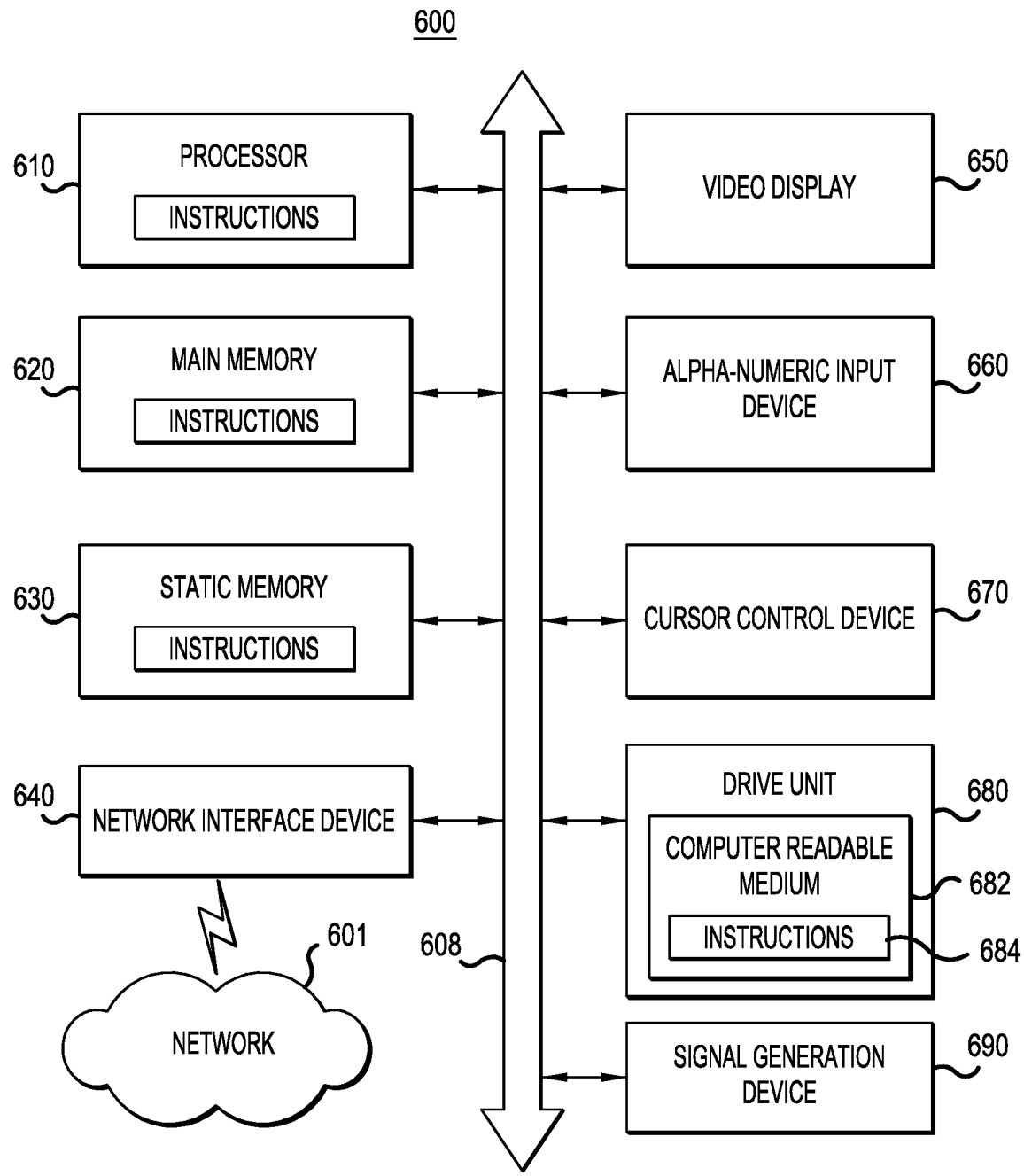
FIG. 6 illustrates a general computer system, on which a method for intraoperative virtual annotation in VATS and minimally invasive surgery is implemented, in accordance with another representative embodiment

FIG. 6 illustrates a general computer system, on which methods of interactive endoscopy for intraoperative virtual annotation in VATS and minimally invasive surgery can be implemented, in accordance with another representative embodiment.

The computer system 600 of FIG. 6 shows a complete set of components for a communications device or a computer device. However, a "controller" as described herein may be implemented with less than the set of components of FIG. 6, such as by a memory and processor combination. The computer system 600 may include some or all elements of one or more component apparatuses in an interactive annotation system described herein, although any such apparatus may not necessarily include one or more of the elements described for the computer system 600 and may include other elements not described.

Referring to FIG. 6, the computer system 600 includes a set of software instructions that can be executed to cause the computer system 600 to perform any of the methods or computer-based functions disclosed herein. The computer system 600 may operate as a standalone device or may be connected, for example, using a network 601, to other computer systems or peripheral devices. In embodiments, a computer system 600 performs logical processing based on digital signals received via an analog-to-digital converter.

In a networked deployment, the computer system 600 operates in the capacity of a server or as a client user computer in a server-client user network environment, or as a peer computer system in a peer-to-peer (or distributed) network environment. The computer system 600 can also be implemented as or incorporated into various devices, such as a stationary computer, a mobile computer, a personal computer (PC), a laptop computer, a tablet computer, or any other machine capable of executing a set of software instructions (sequential or otherwise) that specify actions to be taken by that machine. The computer system 600 can be incorporated as or in a device that in turn is in an integrated system that includes additional devices. In an embodiment, the computer system 600 can be implemented using electronic devices that provide voice, video or data communication. Further, while the computer system 600 is illustrated in the singular, the term "system" shall also be taken to include any collection of systems or sub-systems that individually or jointly execute a set, or multiple sets, of software instructions to perform one or more computer functions.

As illustrated in FIG. 6, the computer system 600 includes a processor 610. The processor 610 may be considered a representative example of the processor 52210 of the controller 522 in FIG. 5B, and executes instructions to implement some or all aspects of methods and processes described herein. The processor 610 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 610 is an article of manufacture and/or a machine component. The processor 610 is configured to execute software instructions to perform functions as described in the various embodiments herein. The processor 610 may be a general-purpose processor or may be part of an application specific integrated circuit (ASIC). The processor 610 may also be a microprocessor, a microcomputer, a processor chip, a controller, a microcontroller, a digital signal processor (DSP), a state machine, or a programmable logic device. The processor 610 may also be a logical circuit, including a programmable gate array (PGA), such as a field programmable gate array (FPGA), or another type of circuit that includes discrete gate and/or transistor logic. The processor 610 may be a central processing unit (CPU), a graphics processing unit (GPU), or both. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 600 further includes a main memory 620 and a static memory 630, where memories in the computer system 600 communicate with each other and the processor 610 via a bus 608. Either or both of the main memory 620 and the static memory 630 may be considered representative examples of the memory 52220 of the controller 522 in FIG. 5B, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 620 and static memory 630 are articles of manufacture and/or machine components. The main memory 620 and static memory 630 are computer-readable mediums from which data and executable software instructions can be read by a computer (e.g., the processor 610). Each of the main memory 620 and static memory 630 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 600 further includes a video display unit 650, such as a liquid crystal display (LCD), an organic light emitting diode (OLED), a flat panel display, a solid-state display, or a cathode ray tube (CRT), for example. Additionally, the computer system 600 includes an input device 660, such as a keyboard/virtual keyboard or touch-sensitive input screen or speech input with speech recognition, and a cursor control device 670, such as a mouse or touch-sensitive input screen or pad. The computer system 600 also optionally includes a disk drive unit 680, a signal generation device 690, such as a speaker or remote control, and/or a network interface device 640.

In an embodiment, as depicted in FIG. 6, the disk drive unit 680 includes a computer-readable medium 682 in which one or more sets of software instructions 684 (software) are embedded. The sets of software instructions 684 are read from the computer-readable medium 682 to be executed by the processor 610. Further, the software instructions 684, when executed by the processor 610, perform one or more steps of the methods and processes as described herein. In an embodiment, the software instructions 684 reside all or in part within the main memory 620, the static memory 630 and/or the processor 610 during execution by the computer system 600. Further, the computer-readable medium 682 may include software instructions 684 or receive and execute software instructions 684 responsive to a propagated signal, so that a device connected to a network 601 communicates voice, video or data over the network 601. The software instructions 684 may be transmitted or received over the network 601 via the network interface device 640.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, interactive endoscopy for intraoperative virtual annotation in VATS and minimally invasive surgery effectively transforms the interventional imaging modality from a passive modality into an interactive image-based modality that provides personnel involved in an interventional medical procedure with a user interface, allowing a surgical scene to be digitally tagged during an interventional medical procedure. This allows personnel involved in medical interventions to keep track of anatomical structures once seen and tasks once performed, which helps eliminate excessive and/or redundant exploration. The labeling of the anatomy during the interventional medical procedure may also help maintain data for retrospective review, and for use in feedback for optimizing future interventional medical procedures. Over a long term, the ability to accumulate annotated (e.g., labeled) surgical video may be used in developing machine learning to further improve integration of information and analyses to augment endoscopic surgery. Automatic labeling in particular becomes increasingly functional as more surgical videos are labeled, which in turn is enabled by a user friendly interface for interactive endoscopy. The ability to label intraoperatively has the potential to produce large quantities of labeled endoscopy data. Such volumes of data can in turn be used to improve deformable registration and accurate overlay of preoperative imaging onto the endoscopic view.

A fixed library of virtual labels may also be used in an automation process, so that even without machine learning simple inputs can be supplemented in order to add or remove virtual annotations to raw endoscopic imagery. In an embodiment, original aspects of the endoscopic imagery may be removed, such as by being covered with a virtual annotation in a particular color.

In another example, rather than supplementing a partial input, virtual annotations may be provided under a supervised automatic process. For example, a user may indicate a particular structure of interest on the endoscopic imagery, and the supervised automatic process can identify the structure through classification, delineate boundaries of the structure, identify a location for a virtual label near the structure, and track the structure as it moves. In this embodiment, even a single initial instruction can be used to implement a virtual annotation.

Examples of where intraoperative virtual annotations can be used include lung surgery where a target location is to be reached and possibly removed. Intraoperative virtual annotations can also be used for tumor resection, lymph node dissection and resection, foreign body removal and so on.

Although interactive endoscopy for intraoperative virtual annotation in VATS and minimally invasive surgery has been described with reference to several exemplary embodiments, it is understood that the words that have been used are words of description and illustration, rather than words of limitation Changes may be made within the purview of the appended claims, as presently stated and as amended, without departing from the scope and spirit of interactive endoscopy for intraoperative virtual annotation in VATS and minimally invasive surgery in its aspects. Although interactive endoscopy for intraoperative virtual annotation in VATS and minimally invasive surgery has been described with reference to particular means, materials and embodiments, interactive endoscopy for intraoperative virtual annotation in VATS and minimally invasive surgery is not intended to be limited to the particulars disclosed; rather interactive endoscopy for intraoperative virtual annotation in VATS and minimally invasive surgery extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A controller for live annotation of interventional imagery, the controller comprising:
 a processor in communication with memory, the processor configured to:
  receive interventional imagery during an intraoperative intervention;
  automatically analyze the interventional imagery for detectable features;
  detect a detectable feature in the interventional imagery;
  determine to add an annotation to the interventional imagery for the detectable feature;
  identify, based on inputting the detectable feature to machine learning, an optimized location to add the annotation to the interventional imagery;

add the annotation to the interventional imagery at the identified optimized location to correspond to the detectable feature;

output, during the intraoperative intervention, a video output based on the interventional imagery and the annotation, the video output including the annotation overlaid on the interventional imagery at the identified optimized location; and apply the machine learning to the video output to obtain quantitative metrics of at least one of (i) one or more features in the video output and (ii) one or more annotations in the video output, wherein addition of the annotation at the optimized location in the video output is based on the quantitative metrics from the machine learning from previous applications of the machine learning to previous video output.

2. The controller of claim 1, wherein the processor is further configured to:

detect an anatomical structure as the detectable feature; and delineate boundaries of the anatomical structure.

3. The controller of claim 1, wherein the processor is further configured to:

detect an interventional tool as the detectable feature; and delineate boundaries of the interventional tool.

4. The controller of claim 1, wherein the processor is further configured to:

identify predetermined information for the detectable feature from a source external to the controller; and add the predetermined information from the source into the interventional imagery as the annotation, wherein the annotation comprises a virtual label for virtually labelling the detectable feature with the predetermined information.

5. The controller of claim 1, wherein the processor is further configured to:

detect an anatomical structure as the detectable feature;

label the anatomical structure with a virtual label as the annotation added to the interventional imagery;

track movement of the anatomical structure relative to an endoscope that generates the video output;

detect movement of the anatomical structure relative to the endoscope that generates the video output; and automatically adjust a position and an orientation of the virtual label based on detecting movement of the anatomical structure relative to the endoscope.

6. The controller of claim 1, wherein the processor is further configured to:

detect and track, using a first algorithm, low-level features in the interventional imagery;

extract the low-level features; and recognize and classify, using a second algorithm, an anatomical structure as the detectable feature in the interventional imagery based on the extracted low-level features.

7. The controller of claim 1, wherein the processor is further configured to:

automatically analyze the interventional imagery for the detectable features in response to a first instruction;

automatically identify the location for the annotation in response to a second instruction; and automatically add the annotation to the interventional imagery at the identified location in response to a third instruction.

8. The controller of claim 1, wherein the processor is further configured to:

automatically add the annotation to the interventional imagery at the identified location in response to an instruction to add the annotation.

9. The controller of claim 1, wherein the processor is further configured to:

automatically identify a location for the annotation in response to an instruction to identify the location.

10. The controller of claim 1, wherein the processor is further configured to:

automatically detect a structure for virtual labelling in response to an instruction to detect the structure.

11. The controller of claim 1, wherein the processor is further configured to:

detect movement of an anatomical structure relative to an endoscope that generates the interventional imagery; and automatically adjust a position and an orientation of the annotation based on the detected movement of the anatomical structure relative to the endoscope.

12. The controller of claim 1, wherein the processor is further configured to:

analyze intraoperative information from the intraoperative intervention;

derive content for the annotation based on the intraoperative information; and add the content into the interventional imagery as the annotation, wherein the annotation comprises a virtual label.

13. The controller of claim 1, wherein the processor is further configured to:

obtain a preoperative segmented model of an anatomical structure;

receive an instruction to annotate the anatomical structure with the preoperative segmented model as the annotation; and virtually replace the anatomical structure in the interventional imagery with the preoperative segmented model of the anatomical structure.

14. The controller of claim 13, wherein the processor is further configured to:

register the preoperative segmented model of the anatomical structure to the anatomical structure; and select an icon corresponding to the preoperative segmented model.

15. The controller of claim 1, wherein the processor is further configured to:

detect a trigger during the intraoperative intervention; and vary the annotation based on the detected trigger.

16. A system for live annotation of interventional imagery, the system comprising:

a display configured to display the interventional imagery;

a processor in communication with memory, the processor configured to:

receive interventional imagery during an intraoperative intervention, automatically analyze the interventional imagery for detectable features, detect a detectable feature in the interventional imagery, determine to add an annotation to the interventional imagery for the detectable feature, identify, based on inputting the detectable feature to machine learning, an optimized location to add the annotation in the interventional imagery, add the annotation to the interventional imagery at the identified optimized location to correspond to the detectable feature, output, during the intraoperative intervention, a video output on the display based on the interventional imagery and the annotation, the video output including the annotation overlaid on the interventional imagery at the identified location, and apply the machine learning to the video output to obtain quantitative metrics of at least one of (i) one or more features in the video output and (ii) one or more annotations in the video output, wherein addition of the annotation at the optimized location in the video output is based on the quantitative metrics from the machine learning from previous applications of the machine learning to previous video outputs.

17. The system of claim 16, wherein the processor is further configured to:
detect the detectable feature and identify the location to add the annotation based on applying machine learning trained from results from at least one previous instantiation of live annotation.

18. A non-transitory computer readable storage medium storing a computer program comprising instructions which, when executed by a processor, cause the processor to:
receive interventional imagery during an intraoperative intervention;
automatically analyze the interventional imagery for detectable features;
detect a detectable feature in the interventional imagery;
determine to add an annotation to the interventional imagery for the detectable feature;
identify, based on inputting the detectable feature to machine learning, an optimized location to add the annotation in the interventional imagery;
add the annotation to the interventional imagery at the identified optimized location to correspond to the detectable feature;

output, during the intraoperative intervention video output based on the interventional imagery and the annotation, the video output including the annotation overlaid on the interventional imagery at the identified optimized location;

apply the machine learning to the video output to obtain quantitative metrics of at least one of (i) one or more features in the video output and (ii) one or more annotations in the video output, wherein addition of the annotation at the optimized location in the video output is based on the quantitative metrics from the machine learning from previous applications of the machine learning to previous video output.

19. The non-transitory computer readable storage medium of claim 18, wherein the instruction, when executed by the processor, further cause the processor to:
detect the detectable feature and identify the location to add the annotation based on applying machine learning trained from results from at least one previous instantiation of live annotation.

20. The non-transitory computer readable storage medium of claim 18, wherein instruction, when executed by the processor, further cause the processor to:
detect an anatomical structure as the detectable feature;
label the anatomical structure with a virtual label as the annotation added to the interventional imagery;
track movement of the anatomical structure relative to an endoscope that generates the video output;
detect movement of the anatomical structure relative to the endoscope that generates the video output; and
automatically adjust a position and an orientation of the virtual label based on detecting movement of the anatomical structure relative to the endoscope.

* * * * *